United States Patent [19]

Hester, Jr.

[11] 4,226,772
[45] Oct. 7, 1980

[54] 1-[(DIALKYLAMINO)METHYL]-6-PHENYL-4H-S-[4,3,-A][1,4]TRIAZOLOBENZODIAZEPINE $N^1$-OXIDE

[75] Inventor: Jackson B. Hester, Jr., Galesburg, Mich.

[73] Assignee: The Upjohn Company, Kalamazoo, Mich.

[21] Appl. No.: 940,802

[22] Filed: Sep. 8, 1978

Related U.S. Application Data

[60] Continuation of Ser. No. 853,290, Nov. 21, 1977, abandoned, which is a continuation-in-part of Ser. No. 713,923, Aug. 12, 1976, abandoned, which is a division of Ser. No. 666,902, Mar. 15, 1976, Pat. No. 4,008,175.

[51] Int. Cl.$^3$ .............................................. A61K 31/55
[52] U.S. Cl. .................................. 260/245.5; 424/269
[58] Field of Search .......... C07D/487/04; 260/308 R, 260/245.5

[56] References Cited

U.S. PATENT DOCUMENTS

| 2,500,131 | 3/1950 | Linsker | 260/279 H |
| 2,518,130 | 8/1950 | Evans et al. | 260/289 H |
| 3,681,343 | 8/1972 | Hester | 260/308 R |
| 3,842,090 | 10/1974 | Gall et al. | 260/308 R |

OTHER PUBLICATIONS

Smith, Open–Chain Nitrogen Compounds, vol. 2, (W. A. Benjamin, Inc., New York, 1966), p. 28.

Merck Index, (9th Edition, Merck & Co., Inc., 1976), pp. 264, 394.

Primary Examiner—O
Assistant Examiner—Alton D. Rollins
Attorney, Agent, or Firm—Hans L. Berneis; Robert A. Armitage; Lawrence T. Welch

[57] ABSTRACT

The compound of the formula

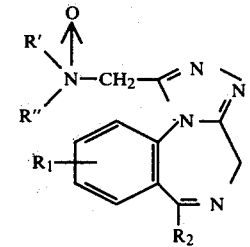

wherein R' and R" are alkyl of 1 to 3 carbon atoms, inclusive; wherein $R_1$ is hydrogen, fluoro, chloro, bromo, nitro, trifluoromethyl or alkylthio in which the alkyl moiety is of 1 to 3 carbon atoms, inclusive; and wherein $R_2$ is phenyl, o-chlorophenyl, o-fluorophenyl, or 2,6-difluorophenyl, is prepared by reacting a 1-halomethyl-6-phenyl-4H-s-triazo[4,3-a][1,4]-benzodiazepine with N,N-dimethylhydroxylamine and a strong base. The compound II and its pharmacologically acceptable acid addition salts have sedative and tranquilizing activity.

5 Claims, No Drawings

1-[(DIALKYLAMINO)METHYL]-6-PHENYL-4H-S-[4,3,-A][1,4]TRIAZOLOBENZODIAZEPINE N¹-OXIDE

CROSS REFERENCE

This is a continuation of pending prior application Ser. No. 853,290, filed Nov. 21, 1977, abandoned, which is a continuation-in-part of prior application Ser. No. 713,923, filed Aug. 12, 1976 (now abandoned), which is a divisional of prior application Ser. No. 666,902, filed Mar. 15, 1976, now U.S. Pat. No. 4,009,175, (Feb. 22, 1977).

BACKGROUND OF THE INVENTION

1. Field of the Invention

This invention is directed to new 1-[(dialkylamino)methyl]-6-phenyl-4H-s-triazolo[4,3-a][1,4]-benzodiazepine N¹-oxides.

The novel compound and the processes of the production therefor can be illustratively represented as follows:

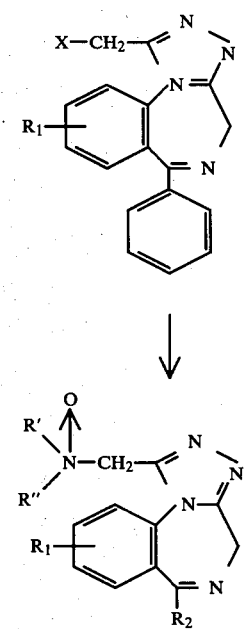

wherein X is chlorine or bromine; wherein R' and R" are alkyl of 1 to 3 carbon atoms, inclusive; wherein $R_1$ is hydrogen, fluoro, chloro, bromo, nitro, trifluoromethyl or alkylthio in which the alkyl moiety is of 1 to 3 carbon atoms, inclusive; and wherein $R_2$ is phenyl, o-chlorophenyl, o-fluorophenyl, or 2,6-difluorophenyl.

The invention also embraces the pharmacologically acceptable addition salts of the compounds II.

The new compounds are remarkable as they show a different spectrum of activity from the known parent compounds without the N-oxide group, namely:

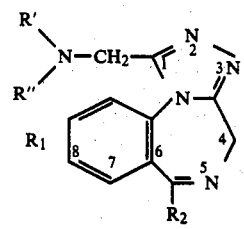

wherein R', R", $R_1$ and $R_2$ have the definitions above listed, which is generically claimed and disclosed in British Pat. No. 1,331,015, sealed Jan. 16, 1974, and specifically disclosed in U.S. Pat. No. 3,842,090, issued Oct. 15, 1974. While these compounds III above have sedative, tranquilizing and antidepressant activity, the N¹-oxide compounds II thereof only have sedative-tranquilizing activity, i.e., a split activity.

The compound 1-[(dimethylamino)ethyl]-8-chloro-6-phenyl-4H-s-[4,3-a][1,4]benzodiazepine (U.S. Pat. Nos. 4,012,413 and 3,759,943) has a particularly strong antidepressant activity with sedative activity lesser than commercial tranquilizers and thus differs from both compounds of formulae II and III. Finally, U.S. Pat. No. 3,681,343, issued Aug. 1, 1972, discloses an N-oxide generically prepared by direct oxygenation with a peracid. U.S. Pat. No. 3,681,343 was reissued as U.S. Pat. No. Re. 28505 Aug. 5, 1975, without the generic or any specific claims to N⁵-oxide compounds.

DESCRIPTION OF THE PREFERRED EMBODIMENT

The more preferred compounds of this invention are of the formula IIA:

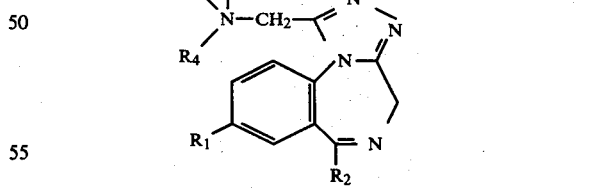

wherein $R_1$ is hydrogen, fluoro, chloro, bromo, nitro, trifluoromethyl, or alkylthio in which the alkyl moiety is of 1–3 carbon atoms, inclusive; wherein $R_2$ is phenyl, o-chlorophenyl, o-fluorophenyl or 2,6-difluorophenyl; and, wherein $R_4$ is methyl or ethyl, or the pharmaceutically acceptable acid addition salts thereof.

The most preferred compounds of this invention are of the formula IIB:

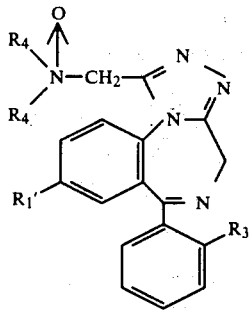

wherein $R'_1$ is hydrogen, fluoro, chloro, or trifluoromethyl; wherein $R_3$ is hydrogen, chloro, or fluoro; and wherein $R_4$ is methyl or ethyl or the pharmacologically acceptable acid addition salts thereof.

The compounds of formula II (IIA and IIB included) 1-[(dialkylamino)methyl]-6-phenyl-4H-s-[4,3-a][1,4]-benzodiazepine $N^1$-oxides, are useful as anti-anxiety, tranquilizing and sedative agents in man and birds.

Single dosages of 0.1–5 mg/kg are useful to sedate small animals, less than 5 kg. particularly during transportation. Larger animals and man require dosages on the low side per kilogram, 0.05 to 1 mg/kg preferably, and this dosage is particularly indicated for anxieties.

The compounds can also be administered as the pharmacologically acceptable acid addition salts of compounds II, which include the hydrochloride, hydrobromide, hydriodide, sulfate, phosphate, acetate, propionate, lactate, maleate, malate, succinate, tartrate, and the like.

The tranquilization and sedative activity of the compounds II was determined in the following rigorous test system for minor tranquilizers.

MINOR TRANQUILIZER TESTS

Antagonism of Pentylenetetrazol(Metrazol ®)-Induced Tonic Seizures

In this procedure, a group of 4 CF-1 mice (Carworth Farms) (18–22 gm each) is injected i.p. with the test compound prepared in 0.25% methylcellulose. Multiple dose levels decreasing in 0.3 log intervals are used. After 30 minutes, pentylenetetrazole is injected s.c. at 85 mg/kg. Fifteen minutes after the pentylenetetrazole, a set of keys is rattled over the cage. The number of mice protected from the tonic extensor seizures is used as a quantal response. The $ED_{50}$ is calculated using the method of Spearman and Karber: Finney, D. J., Statistical Method in Biological Assay, Hafner Publ. Co., N.Y., p 524, 1952). This test is useful for detecting minor tranquilizer and/or anti-convulsant activity.

Protection Against Bicucullin-Induced T.E. Convulsions

In this procedure, groups of 4 CF-1 male mice, weighing 18–22 gm each, are injected i.p. with the test agent prepared in 0.25% methylcellulose. Thirty minutes later, bicucullin is injected i.v. at 1 mg/kg. Bicucullin (Pierce Chem. Co.) is solubilized in 1 N HCl and diluted to a concentration of 1–4 mg/ml with physiological saline and adjusted to a final pH of 5–6 before injection. Mice are observed for 5 minutes after bicucullin injection. A compound is considered to be active if it protects at least 2 of the 4 mice from tonic extensor convulsions during this period. Active compounds are retested using multiple dose levels decreasing at 0.3 log intervals. The number of mice failing to convulse is used as a quantal response to calculate the $ED_{50}$ (Spearman and Karber: Finney, D. J., Statistical Method in Biological Assay, Hafner Publ. Co., N.Y., p 524, 1952). This procedure is a useful test for detecting compounds with minor tranquilizer or sedative activity.

Gamma Butyrolactone Sleep Potentiation

Gamma butyrolactone produces loss of righting in mice at doses higher than 400 mg/kg i.p. At lower doses (200 mg/kg) the mice do not lose their righting reflex unless previously treated with subhypnotic doses of CNS (Central Nervous System) depressing agents. This then provides a technique to study the depressant activity of potential CNS agents.

Groups of 4 male CF-1 mice, weighing 18–22 gm. each, are injected i.p. with the test agent prepared in 0.25% methylcellulose. Thirty minutes later, gamma butyrolactone prepared in the same vehicle is injected i.p. at 200 mg/kg. A compound is considered active if at least 2 of the 4 mice have lost the righting reflex. Active compounds are retested using multiple dose levels decreasing at a 0.3 log interval and the number of mice with loss of righting is used as a quantal response to calculate the $ED_{50}$ (Spearman and Karber: Finney, D. J., Statistical Method in Biological Assay, Hafner Publ. Co., N.Y., p 524, 1952).

The pharmaceutical forms of compounds II or salts thereof contemplated by this invention include pharmaceutical compositions suited for oral, parenteral, and rectal use, e.g., tablets, powder packets, cachets, dragees, capsules, solutions, suspensions, sterile injectable forms, suppositories, bougies, and the like. Suitable diluents or carriers such as carbohydrates, lactose, proteins, lipids, calcium phosphate, cornstarch, stearic acid, methylcellulose and the like may be used as carriers or for coating purposes. Water or oils such as coconut oil, sesame oil, safflower oil, cottonseed oil, and peanut oil, may be used for preparing solutions or suspensions of the active drug. Sweetening, coloring and flavoring agents may be added.

For mammals, food premixes with starch, oatmeal, dried fishmeat, fishmeal, flour, and the like can be prepared.

EXAMPLE 1

8-chloro-1-[(dimethylamino)methyl]-6-phenyl-4H-s-triazolo[4,3-a][1,4]benzodiazepine, $N^1$-oxide and hydrate A stirred solution of N,N-dimethylhydroxylamine (3.67 g, 0.06 mole) in dry dimethylformamide (50 ml) is cooled in an ice bath, under nitrogen, and treated with a 57% mineral oil suspension of sodium hydride (0.84 g, 0.02 mole). The mixture is kept at ambient temperature for 1 hour (a precipitate formed) and then cooled in an ice bath and treated with 8-chloro-1-(chloromethyl)-6-phenyl-4H-s-triazolo[4,3-a][1,4]-benzodiazepine (6.86 g, 0.02 mole). The mixture is kept at ambient temperature for 2 hours and concentrated in vacuo. Last traces of dimethylformamide are removed from the residue by the successive addition and distillation with xylene, toluene, and benzene. The resulting material is chromatographed on silica gel (250 g) with methanol. The product thus obtained is crystallized from methanol-ethyl acetate (following activated charcoal treatment) to give 8-chloro-1-[(dimethylamino)methyl]-6- phenyl-4H-s-triazolo[4,3-a][1,4]benzodiazepine, N¹-oxide, hydrate in three crops: 3.377 g of melting point 160.5°–162.5° C.; 1.145 g of melting point 160°–162° C.; and 0.785 g of melting point 160°–162° C. The analytical sample had a melting point of 157.5°–158.5° C. with decomposition.

Anal. calcd. for $C_{19}H_{18}ClN_5O$: C, 62.04; H, 4.93; Cl, 9.64; N, 19.04. Found: C, 59.89; H, 5.15; Cl, 8.69; 9.35; N, 18.77; $H_2O$, 3.22. Anal. calcd. for 3.22% $H_2O$; C, 61.88; H, 4.96; Cl, 8.98; 9.66; H, 19.39.

Heating at 95° C. in a vacuo of 10 mm Hg 8-chloro-1-[(dimethylamino)methyl]-6-phenyl-4H-s-triazolo-[4,3-a][1,4]benzodiazepine N¹-oxide hydrate for 48 hours gave the unhydrated product.

The same final product will be obtained if 1-(bromomethyl)-8-chloro-6-phenyl-4H-s-triazolo-[4,3-a][1,4]benzodiazepine is employed as reactant.

EXAMPLE 2

8-Chloro-1-[(diethylamino)methyl]-6-phenyl-4H-s-triazolo[4,3-a][1,4]benzodiazepine, N¹-oxide, hydrate A stirred, ice cold solution of N,N-diethylhydroxylamine (50 ml.) in dimethylformamide (50 ml.) under nitrogen, was treated with a 57% suspension of sodium hydride in mineral oil (1.39 g., 0.033 mole). The mixture was kept at ambient temperature for 55 minutes, cooled in an ice bath and treated with 8-chloro-1-(chloromethyl)-6-phenyl-4H-s-triazolo[4,3-a][1,4]benzodiazepine (10.3 g., 0.03 mole). This mixture was kept at ambient temperature for 18 hours and poured into ice water. The resulting mixture was saturated with sodium chloride and extracted with chloroform. The extract was washed with brine, dried over anhydrous sodium sulfate and concentrated. The residue was mixed with xylene and concentrated in vacuo, the resulting material was crystallized from wet methanol-ethyl acetate to give 8-chloro-1-[(diethylamino)methyl]-6-phenyl-4H-s-triazolo[4,3-a][1,4]benzodiazepine, N¹-oxide dihydrate in two crops: 5.91 g., of melting point 137.5°–139.5° C. dec. and 1.16 g., of melting point 135°–137.5° C. The analytical sample had a melting point of 135°–137.5° C. dec.

Anal. calcd. for $C_{21}H_{28}ClN_5O_3$: C, 58.40; H, 6.07; Cl, 8.21; N, 16.22; $H_2O$, 8.3. Found: C, 58.22; H, 6.00; Cl, 8.17; N, 16.28; $H_2O$, 7.8.

EXAMPLE 3

8-Chloro-1-[(diethylamino)methyl]-6-(o-chlorophenyl)-4H-s-triazolo[4,3-a][1,4]benzodiazepine N¹-oxide In the manner given in Example 1, 8-chloro-1-(chloromethyl)-6-(o-chlorophenyl)-4H-s-triazolo-[4,3-a][1,4]benzodiazepine is treated with a cold mixture of N,N-diethylhydroxylamine and sodium hydride in dimethylformamide to give 8-chloro-1-[(diethylamino)methyl]-6-(o-chlorophenyl)-4H-s-triazolo[4,3-a][1,4]benzodiazepine N¹-oxide.

EXAMPLE 4

8-Chloro-1-[(dimethylamino)methyl]-6-(o-chlorophenyl)-4H-s-triazolo[4,3-a][1,4]benzodiazepine N¹-oxide In the manner given in Example 2, a solution of N,N-dimethylhydroxylamine in dimethylformamide is treated with sodium hydride suspended in mineral oil, and the mixture is treated with 8-chloro-1-(bromomethyl)-6-(o-chlorophenyl)-4H-s-triazolo[4,3-a][1,4]benzodiazepine to give 8-chloro-1-[(dimethylamino)methyl]-6-(o-chlorophenyl)-4H-s-triazolo[4,3-a][1,4]benzodiazepine N¹-oxide.

EXAMPLE 5

8-Fluoro-1-[(ethylmethylamino)methyl]-6-phenyl-4H-s-triazolo[4,3-a][1,4]benzodiazepine N¹-oxide In the manner given in Example 1, 8-fluoro-1-(chloromethyl)-6-phenyl-4H-s-triazolo[4,3-a][1,4]benzodiazepine is treated with a cold mixture of N-ethyl-N-methylhydroxyamine and sodium hydride in dimethylformamide to give 8-fluoro-1-[(ethylmethylamino)methyl]-6-phenyl-4H-s-triazolo[4,3-a][1,4]benzodiazepine N¹-oxide.

EXAMPLE 6

8-Fluoro-1-[(dimethylamino)methyl]-6-phenyl-4H-s-triazolo[4,3-a][1,4]benzodiazepine N¹-oxide In the manner given in Example 2, a solution of N,N-dimethylhydroxylamine in dimethylformamide is treated with sodium hydride suspended in mineral oil, and the mixture is treated with 8-fluoro-1-(bromomethyl)-6-phenyl-4H-s-triazolo[4,3-a][1,4]benzodiazepine to give 8-fluoro-1-[(dimethylamino)methyl]-6-phenyl-4H-s-triazolo[4,3-a][1,4]benzodiazepine, N¹-oxide.

EXAMPLE 7

8-Trifluoromethyl-1-[(diethylamino)methyl]-6-phenyl-4H-s-triazolo[4,3-a][1,4]benzodiazepine N¹-oxide In the manner given in Example 1, 8-trifluoromethyl-1-(chloromethyl)-6-phenyl-4H-s-triazolo[4,3-a][1,4]benzodiazepine is treated with a cold mixture of N,N-diethylhydroxylamine and sodium hydride in dimethylformamide to give 8-trifluoromethyl-1-[(diethylamino)methyl]-6-phenyl-4H-s-triazolo[4,3-a][1,4]benzodiazepine N¹-oxide.

EXAMPLE 8

8-Nitro-1-[(dimethylamino)methyl]-6-(o-chlorophenyl)-4H-s-triazolo[4,3-a][1,4]benzodiazepine, N¹-oxide In the manner given in Example 2, a solution of N,N-dimethylhydroxylamine in dimethylformamide is treated with sodium hydride, suspended in mineral oil, and the mixture is treated with 8-nitro-1-(chloromethyl)-6-(o-chlorophenyl)-4H-s-triazolo[4,3-a][1,4]benzodiazepine to give 8-nitro-1-[(dimethylamino)methyl]-6-(o-chlorophenyl)-4H-s-triazolo[4,3-a][1,4]benzodiazepine, N¹-oxide.

EXAMPLE 9

8-Nitro-1-[(dipropylamino)methyl]-6-(o-chlorophenyl)-4H-s-triazolo[4,3-a][1,4]benzodiazepine, N¹-oxide In the manner given in Example 1, 8-nitro-1-(chloromethyl)-6-(o-chlorophenyl)-4H-s-triazolo[4,3-a][1,4]benzodiazepine is treated with a cold mixture of N,N-dipropylhydroxylamine and sodium hydride in dimethylformamide to give 8-nitro-1-[(dipropylamino)methyl]-6-(o-chlorophenyl)-4H-s-triazolo[4,3-a][1,4]benzodiazepine, N¹-oxide.

EXAMPLE 10

8-Nitro-1-[(diisopropylamino)methyl]-6-(o-chlorophenyl)-4H-s-triazolo[4,3-a][1,4]benzodiazepine, $N^1$-oxide In the manner given in Example 2, a solution of N,N-diisopropylhydroxylamine in dimethylformamide is treated with sodium hydride suspended in mineral oil, and the mixture is treated with 8-nitro-1-(chloromethyl)-6-(o-chlorophenyl)-4H-s-triazolo[4,3-a][1,4]benzodiazepine to give 8-nitro-1-[(diisopropylamino)methyl]-6-(o-chlorophenyl)-4H-s-triazolo[4,3-a][1,4]benzodiazepine, $N^1$-oxide.

EXAMPLE 11

8-Bromo-1-[(diethylamino)methyl]-6-(o-chlorophenyl)-4H-s-triazolo[4,3-a][1,4]benzodiazepine, $N^1$-oxide In the manner given in Example 1, 8-bromo-1-(chloromethyl)-6-(o-chlorophenyl)-4H-s-triazolo[4,3-a][1,4]benzodiazepine is treated with a cold mixture of N,N-diethylhydroxylamine and sodium hydride in dimethylformamide to give 8-bromo-1-[(diethylamino)methyl]-6-(o-chlorophenyl)-4H-s-triazolo[4,3-a][1,4]benzodiazepine, $N^1$-oxide.

EXAMPLE 12

8-Bromo-1-[(methylpropylamino)methyl]-6-(o-chlorophenyl)-4H-s-triazolo[4,3-a][1,4]benzodiazepine, $N^1$-oxide In the manner given in Example 2, a solution of N-methyl-N-propylhydroxylamine in dimethylformamide is treated with sodium hydride suspended in mineral oil and the mixture is treated with 8-chloro-1-(bromomethyl)-6-(o-chlorophenyl)-4H-s-triazolo[4,3-a][1,4]benzodiazepine to give 8-bromo-1-[(methylpropylamino)methyl]-6-(o-chlorophenyl)-4H-s-triazolo[4,3-a][1,4]benzodiazepine N-oxide.

The pharmacologically acceptable acid addition salts of the compounds of formula II can be prepared and isolated by conventional processes, such as reacting a compound of said formula with a selected pharmacologically acceptable acid. Such acids include hydrochloric, hydrobromic, phosphoric, sulfuric, acetic, tartaric, lactic, citric, malic, maleic, methanesulfonic, benzenesulfonic, cyclohexanesulfamic acids, toluenesulfonic, and the like. The reaction is conveniently performed in an organic solvent, e.g., ether, dioxane, or tetrahydrofuran, ethanol, methanol, or ethyl acetate; the salts can be recovered by crystallization, precipitation or evaporation of the solvent. These salts are useful in the same manner as the free base.

I claim:

1. A compound of the formula II:

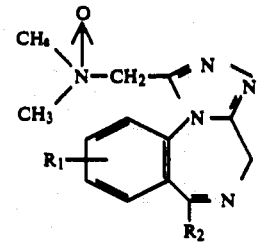

wherein $R_1$ is hydrogen, fluoro, chloro, bromo, nitro, trifluoromethyl or alkylthio in which the alkyl moiety is of 1 to 3 carbon atoms, inclusive; and wherein $R_2$ is phenyl, o-chlorophenyl, o-fluorophenyl, or 2,6-difluorophenyl or the pharmacologically acceptable acid addition salts thereof.

2. Compounds according to claim 1 of the formula IIB:

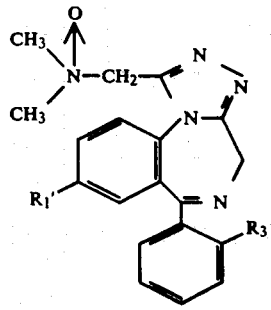

wherein $R'_1$ is hydrogen, fluoro, chloro, or trifluoromethyl; and $R_3$ is hydrogen, chloro, or fluoro, or the pharmacologically acceptable acid addition salts thereof.

3. The compound according to claim 2 wherein $R'_1$ is chloro, $R_3$ is hydrogen, and the compound is therefore 8-chloro-1-[(dimethylamino)methyl]-6-phenyl-4H-s-triazolo[4,3-a][1,4]benzodiazepine $N^1$-oxide.

4. The compound according to claim 2 wherein $R'_1$ and $R_3$ are chloro, and the compound is therefore 8-chloro-1-[(dimethylamino)methyl]-6-(o-chlorophenyl)-4H-s-triazolo[4,3-a][1,4]benzodiazepine $N^1$-oxide.

5. The compound according to claim 2 wherein $R'_1$ is fluoro, $R_3$ is hydrogen, and the compound is therefore 8-fluoro-1-[(dimethylamino)methyl]-6-phenyl-4H-s-triazolo[4,3-a][1,4]benzodiazepine $N^1$-oxide.

UNITED STATES PATENT OFFICE
CERTIFICATE OF CORRECTION

Patent No. 4,226,772    Dated 7 October 1980

Inventor(s) Jackson B. Hester, Jr.

It is certified that error appears in the above-identified patent and that said Letters Patent are hereby corrected as shown below:

Column 2, line 16, "Pat. No. 3,842,090" should read -- Pat. No. 3,942,090 --.
Column 3, line 10, in the formula, "$R_1'$" should read -- $R'_1$ --.
Column 5, line 44, ", 8.3. Found:" should read -- , 8.34.  Found: --.
Column 5, line 45, ", 7.8." should read -- , 7.86. --.
Column 8, line 31, in the formula, "$R_1'$" should read -- $R'_1$ --.
Column 8, line 5, in the formula, "$CH_6$" should read -- $CH_3$ --.

Signed and Sealed this

Tenth Day of August 1982

|SEAL|

Attest:

Attesting Officer

GERALD J. MOSSINGHOFF

Commissioner of Patents and Trademarks